United States Patent [19]

Santi et al.

[11] Patent Number: 5,164,490

[45] Date of Patent: Nov. 17, 1992

[54] PNEUMOCYSTIS CARINII DIHYDROFOLATE REDUCTASE GENE AND METHODS FOR ITS USE

[75] Inventors: Daniel V. Santi; Jeffrey Edman; Ursula Edman, all of San Francisco, Calif.

[73] Assignee: The Regents of the University of California, Oakland, Calif.

[21] Appl. No.: 437,511

[22] Filed: Nov. 15, 1989

[51] Int. Cl.$^5$ .................... C07H 15/12; C12P 21/06; C12P 19/36

[52] U.S. Cl. .................................. 536/27; 435/69.1; 435/91; 435/172.3

[58] Field of Search ................. 536/27; 435/91, 172.3, 435/69.1

[56] References Cited

PUBLICATIONS

Edman, et al., P.N.A.S. 86:8625–8629, 1989.
Trimble, et al., Science 239:1145–1147, 1988.
Nunberg, et al., Cell 19:355–364, 1980.

*Primary Examiner*—John W. Rollins
*Attorney, Agent, or Firm*—Cooley Godward Castro Huddleson & Tatum

[57] ABSTRACT

Genetic material encoding dihydrofolate reductase (DHFR) of *Pneumocystis carinii* has been isolated and characterized. This genetic material allows the production of peptides for use in the design of inhibitors specific for *P. carinii* DHFR (as opposed to DHFR in the host infected with *P. carinii*) or can itself be directly used in hybridization assays.

12 Claims, No Drawings

PNEUMOCYSTIS CARINII DIHYDROFOLATE REDUCTASE GENE AND METHODS FOR ITS USE

BACKGROUND OF THE INVENTION

1. Field of the Invention

This invention relates to the two fields of genetic engineering and drug design and is more particularly related to the identification and preparation of drugs effective in inhibiting a particular purified enzyme, the enzyme being available as a result of genetic engineering of the gene that encodes the peptide.

2. Description of the Background

Pneumocystis carinii pneumonia is a leading cause of morbidity and mortality in acquired immunodeficiency syndrome (AIDS). Since the onset of the AIDS epidemic, the incidence of *P. carinii* pneumonia has risen from approximately 200 cases per year to much greater than 25,000 cases per year in the U.S. Due to the lack of a continuous in vitro culture system and the cumbersome nature of the rat model of *P. carinii* pneumonia, anti-*P. carinii* therapy has been developed largely on the assumption that anti-protozoan agents were likely to be effective. In fact, *P. carinii* has recently been shown to be a member of the Fungi.

The two principal therapeutic modalities, trimethoprim/ sulfamethoxazole and pentamidine, were developed using the anti-protozoan theory. Prior to the AIDS epidemic, these agents were sufficient for treatment of the rare cases of *P. carinii* pneumonia. However, in the HIV-positive patient, therapy and prophylaxis with the standard anti-*P. carinii* agents are complicated by frequent toxic and allergic side effects. New compounds active against *P. carinii* are clearly needed.

The inability to propagate *P. carinii* reliably in vitro and the limited quantities of *P. carinii* enzymes that can be purified from infected rat lungs have hindered the search for anti-*P. carinii* agents. Purification and characterization of the intracellular targets for such agents would enable the development of new therapies of *P. carinii* pneumonia.

Of the known anti-*P. carinii* agents, the dihydrofolate reductase (DHFR) inhibitors are the most thoroughly characterized. DHFR plays a central role in the de novo synthesis of nucleic acid precursors. DHFR inhibitors (e.g., methotrexate, trimethoprim, and pyrimethamine) are effective anti-neoplastic, anti-bacterial, and anti-protozoal agents. *P. carinii* pneumonia clearly responds to the combination of a DHFR inhibitor (trimethoprim or pyrimethamine) and a sulfonamide. However, despite their obvious efficacy when used in conjunction with a sulfonamide, trimethoprim and pyrimethamine are in themselves poor inhibitors of *P. carinii* DHFR [50% inhibitory concentration values ($IC_{50}$) of 39,600 and 2,400 nM respectively compared to 8 and 2,500 nM for *E. coli* DHFR at similar substrate concentrations]. Other antifolates have been shown to be more effective inhibitors of *P. carinii* DHFR, but require concomitant administration of leucovorin to prevent host toxicity. If pure *P. carinii* DHFR were available for study, then inhibitors that surpass the efficacy of the known antifolates could be found by comparing binding affinities of the inhibitor to *P. carinii* DHFR versus mammalian DHFR.

SUMMARY OF THE INVENTION

The present invention provides genetic material encoding the enzyme dihydrofolate reductase (DHFR) from *Pneumocystis carinii*. The genetic material can be used to produce the enzyme for use in the design of drugs that specifically inhibit the DHFR enzyme. Additionally, the genetic material can be used as a source of probes that can be used in nucleic acid hybridization assays for the direct detection of *P. carinii* infections. Specific genetic material and techniques for the identification of drugs that selectively inhibit *P. carinii* DHFR are disclosed in the following detailed description and the examples that follow.

DESCRIPTION OF SPECIFIC EMBODIMENTS

The present inventors have identified and obtained for the first time genetic material encoding dihydrofolate reductase of the fungus *Pneumocystis carinii*, which previously has been available only in limited quantities. Since DHFR is central to the synthesis of nucleic acid precursors, availability of the enzyme in significant quantities in pure form will allow the design of drugs that specifically inhibit the *P. carinii* enzyme relative to the host's DHFR enzyme. Accordingly, identification and isolation of this specified genetic material allows production of *P. carinii* DHFR inhibitors. It also provides a source of nucleic acid probes for use in hybridization techniques that allow direct detection of *P. carinii* infection.

TABLE 1

*P. carinii* DHFR cDNA sequence. The first residue of the predicted start codon is designated nucleotide 1. Nucleotide numbers are presented on the left and amino acid numbers are above the sequence. The 43 bp intron present in the genomic sequence is shown below the cDNA sequence. The single base change present in the genomic clones is shown below the sequence at position 654.

```
                                                                                        1
                                                     Met Asn Gln Lys Ser Leu Thr Ile Val Ala Leu Thr Thr Ser Tyr Gly Ile Arg Ser
 -30   TTTTGTCGACGGACAGTCCGTTTGATTTTG ATG AAT CAG CAA AAG TCT TTA ACA TTG GTT GCA CTT GCA ACT TCT TAT GGA ATT GGC CGA TCA 20                          30                          40                              50
       Asn Ser Leu Pro Trp Lys Leu Lys Ser Tyr Phe Lys Arg Val Thr Ser Phe Val Pro Thr Phe Asp Ser Phe Glu Ser Met
 +67   AAC TCT CTT CCA TGG AAA TTA AAG AGT TAT TTT AAA AGA GTA ACC TCT TTT GTA CCA ACT TTT GAT TCA TTT GAA TCG ATG 60                          70                           80
       Asn Val Val Leu Met Gly Arg Lys Thr Trp Glu Ser Ile Pro Leu Gln Phe Arg Pro Leu Lys Gly Arg Ile Asn Val Val Ile Thr Arg
+157   AAT GTT GTA TTG ATG GGT CGA AAA ACA TGG GAA AGT ATT CCT TTG CAA TTT CGG CCC CTT AAA GGT CGT ATT AAT GTT GTT ATC ACT CGA 90                          100                          110
       Asn Glu Ser Leu Asp Leu Asn Gly Ile His Ser Ala Lys Ser Leu Asp Lys Ile Ala Leu Glu Leu Leu Tyr Arg Thr Tyr Gly Ser Glu
+247   AAT GAA TCT CTG GAT CTA GGA AAT CAT TCT GCA AAA TCC TTG GAT GCT TTG GAA TTG TTA TAT CGT ACA TAT GGT TCT GAA

GCATGTTAAAAAAATTAATCTGAATTCGATTGACAATATTAG 120                          130                         140
       Ser Ser Val Gln Ile Asn Arg Ile Phe Val Ile Gly Gly Ala Gln Leu Tyr Lys Ala Ala Met Asp His Pro Lys Leu Asp Arg Ile Met
+337   AGT TCG GTT CAA ATT AAT CGA ATT TTC GTT ATA GGT GGT GCA CAG CTA TAT AAA GCA GCT ATG GAT CAT CCT AAA TTA GAT AGA ATT ATG 150                          160                          170
       Ala Thr Ile Ile Tyr Lys Asp Ile His Cys Asp Val Phe Phe Pro Leu Lys Phe Arg Asp Lys Trp Ser Ser Val Trp Lys Lys Glu
+427   GCT ACA ATA ATA TAC AAG GAT ATT CAT TGT GAT GTA TTT TTT CCA CTT AAA TTT AGG GAT AAA GAA TGG TCT TCT GTA TGG AAA AAA GAA 180                          190                           200
       Lys His Ser Asp Leu Glu Ser Trp Val Gly Thr Val Lys Val Pro His Gly Lys Ile Asn Glu Asn Gly Phe Asp Tyr Glu Phe Glu Met Trp
+517   AAA CAT TCA GAT TTA GAA TCT TGG GTT ACT AAA GTT CCT CAT GGT AAA ATA AAT GAA GAC GGT TTT GAT TAT GAA TTC GAA ATG TGG

206
       Thr Arg Asp Leu OC
+607   ACA AGA GAT TTA TAA ATCCCTTTCAAATCTTTTTATGGCTTTTAATACTACTAATTCTCTTGTTATTCTATTTATTCAATATTCTAAATTCTTTTTATTTCGAAAACCTTTCGA
                                                                                                       G

+721   TCTACCAATTCAACTCTCTTCATACTTTTGCTATCTCATAACTATAAAAATCCTACATATTAATTACAAAAAAAATATCTATATTCAATTAAACAAAA
```

The invention has specifically contemplated each and every possible variation of polynucleotide that could be made by selecting combinations based on the possible codon choices listed in Table 1 and Table 2 (below), and all such variations are to be considered as being specifically disclosed. Codons in which the third base is A or T are favored in *P. carinii*. However, codons are preferably selected to fit the host cell in which the enzyme is being produced. Selection of codons to maximize expression of proteins in a heterologous host is a known technique.

Other DNA molecules that code for such peptides can readily be determined from the list of codons in Table 2 and are likewise contemplated as being equivalent to the DNA sequence of Table 1. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

TABLE 2

| GENETIC CODE | |
| --- | --- |
| Alanine (Ala, A) | GCA, GCC, GCG, GCT |
| Arginine (Arg, R) | AGA, AGG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamine (Gln, Q) | CAA, CAG |
| Glutamic acid (Glu, E) | GAA, GAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal | TAA, TAG, TGA |

Key: Each 3-letter triplet represents a trinucleotide of DNA having a 5' end on the left and a 3' end on the right. The letters stand for the purine or pyrimidine bases forming the nucleotide sequence: A = adenine, G = guanine, C = cytosine, and T = thymine. The RNA code is the same except that U (uracil) replaces T.

In addition to the specific nucleotides listed in Table 1, DNA (or corresponding RNA) molecules of the invention can have additional nucleotides preceding or following those that are specifically listed. For example, poly A can be added to the 3'-terminal; a short (e.g., fewer than 20 nucleotides) sequence can be added to either terminal to provide a terminal sequence corresponding to a restriction endonuclease site, stop codons can follow the peptide sequence to terminate translation, and the like. Additionally, DNA molecules containing a promoter region or other control region upstream from the gene can be produced. All DNA molecules containing the sequences of the invention will be useful for at least one purpose since all can minimally be fragmented to produce oligonucleotide probes and be used in the isolation or detection of DNA from biological sources.

A number of words used in this specification have specific means in addition to their more common meanings. By "equivalent" is meant, when referring to two nucleotide sequences, that the two nucleotide sequences in question encode the same sequence of amino acids. When "equivalent" is used in referring to two peptides, it means that the two peptides will have a common property (such as enzymatic activity, as established by the context). The property does not need to be present to the same extent in both peptides (e.g., two peptides can exhibit different rates of enzymatic activity), but the properties are preferably substantially the same. "Complementary," when referring to two nucleotide sequences, means that the two sequences are capable of hybridizing, preferably with less than 25%, more preferably with less than 15%, even more preferably with less than 5%, most preferably with no mismatches between opposed nucleotides. Preferred hybridizing conditions (which are not limited to specific numbers of mismatches) are set forth in the Examples. The term "substantially" varies with the context as understood by those skilled in the relevant art and generally means at least 70%, preferably means at least 80%, more preferably at least 90%, and most preferably at least 95%. The term "isolated" as used herein refers to peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acrylamide gel) but not obtained either as pure substances or as solutions. The phrase "replaced by" or "replacement" as used herein does not necessarily refer to any action that must take place but to the peptide that exists when an indicated "replacement" amino acid is present in the same position as the amino acid indicated to be present in a different formula (e.g., when leucine instead of valine is present at amino acid 11).

Since the DNA sequence of the gene has been identified, it is possible to produce a DNA gene entirely by synthetic chemistry, after which the gene can be inserted into any of the many available DNA vectors using known techniques of recombinant DNA technology. Thus, the present invention can be carried out using reagents, plasmids, and microorganisms which are freely available and in the public domain at the time of filing of this patent application without requiring a deposit of genetic material.

For example, nucleotide sequences greater than 100 bases long can be readily synthesized on an Applied Biosystems Model 380A DNA Synthesizer as evidenced by commercial advertising of the same (e.g., Genetic Engineering News, Nov./Dec. 1984, p. 3). Such oligonucleotides can readily be spliced using, among others, the technique of preparing overlapping complementary sequences (e.g, 1-100 of coding strand, 0-50 and 51-150 of complementary strand, 101-200 of coding strand, etc.), followed by hybridizing and ligating the strands. Such techniques are well known and are described in detail in, for example, Davis et al., *Basic Methods in Molecular Biology,* Elsevier Science Publ. Co., Inc., N.Y. (1986). The peptides can then be expressed in a host organism as described herein.

Furthermore, automated equipment is also available that makes direct synthesis of many of the peptides disclosed herein readily available, especially peptide fragments of less than the entire *P. carinii* DHFR enzyme. In the same issue of Genetic Engineering News mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

In addition to the specific polypeptide sequence shown in Table 1, peptide fragments based on this sequence and fragments and full length sequences representing minor variations thereof will have at least some of the biological activities of DHFR and will therefore be useful in drug development or other studies. For example, fragments of the DHFR enzyme sequence can readily be prepared and can be screened for use as binding site models. Peptide synthesizers can be used to prepare small polypeptide fragments (e.g., less than 100 amino acids) or techniques of genetic engineering can be used to prepare larger fragments. A simple screening procedure that will identify suitable polypeptide fragments consists of attaching a DHFR substrate to an affinity column and capturing peptide fragments that are retained by the bound substrate. Such peptides can also be used (and are indeed more likely to be used) as immunogens for the preparation of antibodies or as standards in assays that use antibodies to P. carinii DHFR as a method of identifying the presence of a P. carinii infection.

The ability to prepare and select peptide fragments having appropriate binding affinity from a larger protein is well known in the art and is described in a number of publications, including patents. See, for example, U.S. Pat. No. 4,629,783, which describes the preparation of immunologically active fragments of viral proteins that bind with the same antibodies as the entire viral protein.

In addition, minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e., a conservative replacement) will not have a major effect on the biological activity of the resulting molecule, especially if the replacement does not involve an amino acid at a binding site or other site of biologic activity. This is particularly true of the DHFR enzyme in view of the know significant variations that exist between species. Furthermore, additional amino acids can be present be present at either of the two termini, or amino acids can be absent, from one or both of the termini, as is known in the art.

Whether a change results in a functioning peptide can readily be determined by direct analysis for function in a assay that relies on ability of the modified enzyme (or fragment) to carry out the normal function of the natural DHFR enzyme (or fragment). Peptides in which more than one replacement has taken place can readily be tested in the same manner. Preferred peptides differ at no more than 12, more preferably no more than 5, amino acids in any contiguous group of 20 amino acids. Substitutions of amino acids, when they occur, are preferably from within standard conservative groups. Standard conservative groups of amino acids are shown in parenthesis using the one-letter amino acid code: nonpolar (A,V,L,I,P,M); aromatic (F,T,W); uncharged polar (G,S,T,C,N,Q); acidic (D,E); basic (K,R,H). The aromatic amino acids are sometimes considered to belong to the broader-defined nonpolar (F,W) or uncharged polar (T) groups. However, such modified enzymes are less useful in the specific techniques described below related to identification of species-specific inhibitors of P. carinii DHFR.

Salts of any of the peptides described herein will naturally occur when such peptides are present in (or isolated from) aqueous solutions of various pHs. All salts of peptides having the indicated biological activity are considered to be within the scope of the present invention. Examples include alkali, alkaline earth, and other metal salts of carboxylic acid residues, acid addition salts (e.g., HCl) of amino residues, and zwitter ions formed by reactions between carboxylic acid and amino residues within the same molecule.

Peptides of the invention can be prepared for the first time as homogeneous preparations free of other P. carinii materials, either by direct synthesis or by using a cloned gene or a fragment thereof as described herein. The P. carinii DHFR peptide was previously available in the form of a crude homogenate with a purity of less than 0.1%. This crude preparation was not free of all other P. carinii materials.

Although genes and corresponding proteins can be prepared by the totally synthetic techniques discussed above, in preferred embodiments of the invention genetic information is obtained from natural sources and identified as described herein. The genetic material is first obtained in the form of a gene library, using any of numerous existing techniques. The first of these is to randomly shear genomic DNA and insert this sheared material into expression vectors. If enough recombinants are generated, there is a good probability of having at least one recombinant in the population which is expressing a fusion protein corresponding to the enzyme of interest.

Another strategy for preparing gene libraries is to make complementary DNA (cDNA) copies of the total mRNA population of the organism and to clone these as recombinant molecules in expression vectors. The expected nature of the organism (i.e., it was expected to have the characteristics of a fungus) indicated that introns might be present within the coding region of the desired gene. Although introns do not preclude use of sheared genomic DNA, they increase the number of recombinants which must be screened and make further analyses substantially complicated. Based on this result, use of a cDNA library to obtain P. carinii genes is preferred.

Such a library was generated in the laboratory of the inventors and screened for expression of a gene product conferring trimethoprim resistance on the host. Details of this example are set forth below, including details of the experiments that lead to obtaining the complete sequence of the gene. However, there is no reason to believe that the sequence and specific engineered organism prepared by the inventors is any better than other clones that can be prepared using the guidance set forth in this specification. In fact, it is likely that expression of P. carinii DHFR can be enhanced over that described herein by selection of other expression systems.

Now that the sequence of P. carinii DHFR has been determined, it is no longer necessary to go through these steps to obtain the genetic material of the present invention. The polymerase chain reaction (PCR) technique can now be used to isolate genes from natural sources in a simpler and more direct manner. The PCR technique, including use in diagnosis, is disclosed in U.S. Pat. No. 4,683,202, which is herein incorporated by reference. Since *P. carinii* specimens are readily available from sources such as the American Type Culture Collection of Rockville, Md., and since PCR probes can be prepared using the sequences set forth in this specification, it is possible to obtain any desired segment of the sequences set forth herein using the PCR technique and commercially available sources of the *P. carinii* genomic material. A specific example of such a technique for isolating the *P. carinii* DHFR chromosomal gene is described in the examples that follow.

Although the techniques set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of *P. carinii* protein can be enhanced by including multiple copies of the gene in a transformed host; by selecting a vector known to reproduce in the host, thereby producing large quantities of protein from exogenous inserted DNA (such as pUC8; ptac12; pIN-III-ompA1, 2, or 3; pOTS; pAS1; or pKK223-3); or by any other known means of enhancing peptide expression.

One common variation is the preparation of a polypeptide of the invention in the form of a fused polypeptide. Such peptides are typically prepared by using the promoter region of a gene known to be expressed in a host and inserting nucleotides that encode all or a major portion of the amino acid sequence of the invention into the genetic sequence for the host protein. Examples of such fused proteins include $\beta$-galactosidase fused proteins. If desired, the fused peptide can be designed so that a site recognized by a proteolytic enzyme is present at the junction between the two fused proteins. The proteolytic enzyme can then be used to cleave the expressed protein so that the desired DHFR enzyme is available in pure form.

In all cases, a *P. carinii* protein will be expressed when the DNA sequence is functionally inserted into the vector. By "functionally inserted" is meant in proper reading frame and orientation, as is well understood by those skilled in the art. Typically, a gene will be inserted downstream from a promoter and will be followed by a stop codon, although production as a hybrid protein (possibly followed by cleavage) may be used, if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

The implications of the present invention are significant in that useful amounts of *P. carinii* DHFR and genetic material of the invention will become available for use in the development of hybridization assays or in any other type of assay utilizing these materials as a reagent for use in diagnosis, immunization, therapeutics, and research. Transferring the *P. carinii* cDNA which has been isolated to other expression vectors will produce constructs which improve the expression of a *P. carinii* DHFR in *E. coli* or express the polypeptide in other hosts.

Particularly contemplated is the isolation of genes from other strains of *P. carinii* using oligonucleotide probes based on the principal and variant nucleotide sequences disclosed herein. Such probes can be considerably shorter than the entire sequence but should be at least 10, preferably at least 14, nucleotides in length. Intermediate oligonucleotides from 20 to 500, especially 30 to 200, nucleotides in length provide particularly specific and rapid-acting probes. Longer oligonucleotides are also useful, up to the full length of the gene. Both RNA and DNA probes can be used.

In use, the probes are typically labelled in a detectable manner (e.g., with $^{32}P$, $^{3}H$, biotin, or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known.

Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

In summary, *P. carinii* DHFR cDNA sequences have been isolated by direct expression in *E. coli*. The open-reading frame of this gene directs the synthesis of a 23,868 dalton protein with identifiable similarities to known DHFRs. In at least one case, the *P. carinii* DHFR gene contains an intron of 43 bp. The DNA sequences are A-T rich and demonstrate a market bias toward codons containing these residues in the third position. *P. carinii* DHFR is not found as a bifunctional enzyme with thymidylate synthase (TS). Chromosomal localization demonstrates that DHFR is not genetically linked to TS, as is found in protozoans. *P. carinii* DHFR has been expressed in large quantities in *E. coli*, which provides a source of pure enzyme for future studies. Furthermore, DNA sequence analysis shows that human *P. carinii* DHFR is identical to the enzyme from rat. Immune-suppressed rats are the only available non-human models for developing drugs for treatment of humans with *P. carinii*-specific DHFR inhibitors.

The marked sequence differences between microbial and human DHFRs have made this enzyme an important target for antimicrobial chemotherapy, as exemplified by the widely used antimicrobials, trimethoprim and pyrimethamine. Trimethoprim in combination with sulfamethoxazole is one of the major therapeutic and prophylactic regimens for *P. carinii* pneumonia. Surprisingly, the trimethoprim component is a very poor inhibitor of *P. carinii* DHFR, showing an $IC_{50}$ value 10,000-fold higher than with the *E. coli* enzyme. Moreover, the drug inhibits the host DHFR more potently than the target *P. carinii* enzyme. Several speculations arise from this finding. First, it is clear that the sulfa component of the trimethoprimsulfamethoxazole combination plays a major role in the efficacy towards *P. carinii*. This is supported by the lack of efficacy of trimethoprim alone in the treatment of the rat model of *P. carinii* infection, and the known synergism of trimethoprim and sulfa drugs. Second, it is likely that trimethoprim is not the optimal DHFR inhibitor to be used in the treatment of *P. carinii*. Finally, with the availability of large amounts of recombinant *P. carinii* DHFR provided by this invention, it should not be difficult to surpass the efficacy of trimethoprim. This can be accomplished simply by screening the available collections of anti-folates (and new compounds as they are developed) and avoiding classes of compounds which inhibit the human enzyme while selecting classes that inhibit the *P. carinii* enzyme. *P. carinii* DHFR also represents a promising target for drug design based upon molecular structure.

It will be recognized that the technique described in the preceding paragraph is an initial screening process and does not provide a definitive answer to the question of whether a particular compound can be used to treat infected humans. Other factors, such as toxicity and stability, must also be considered. However, if a molecule is not a potent inhibitor of *P. carinii* DHFR or does show species-specific selectivity, it is unlikely that the molecule will effective by this modality. The screening technique therefore is an important first step in the development of a commercial treatment of *P. carinii* pneumonia.

The invention now being generally described, the same will be better understood by reference to the following examples which are provided for purposes of illustration only and are not to be considered limiting of the invention unless so specified.

EXAMPLES

Bacterial strains and media

*E. coli* strains XL1B and HB101 were used as a bacteriophage lambda and plasmid hosts. The DHFR-deficient strain D3-157 used for expression experiments was obtained from Sara Singer and has been previously described; see Singer et al., *J. Bacteriol.* (1985) 164:470-472. Other publicly available strains can be used if desired. *E. coli* JM101 and M13 vectors were used for DNA sequencing. Media used was Luria broth plus appropriate antibiotics (ampicillin 100 μg/ml and/or trimethoprim 100 μg/ml).

*Pneumocystis carinii* preparations

*P. carinii* from steroid-treated rats and human *P. carinii* from autopsy samples were prepared as described in Kovacs et al., *J. Immunol.* (1988) 140:2023-2031.

*Pneumocystis carinii* DNA libraries and phagemid rescue

A rat *P. carinii* cDNA library in the bacteriophage lambda vector ZAP (Stratagene) was constructed in the following manner. Phagemids were rescued from the library for co-infection of *E. coli* XL1B with $8 \times 10^7$ plaque-forming units (pfu) of lambda phage and $2 \times 10^9$ pfu of R408 helper phage in 45 mls of Luria broth. After four hours at 37° C., the culture was heated to 70° C. for 30 minutes and clarified by centrifugation, and the supernatant containing rescued phagemid was saved. The supernatant had a titer of $4 \times 10^4$ ampicillin-resistant colony forming units per microliter.

Transverse alternating field electroporesis of *P. carinii* chromosomes

*P. carinii* chromosomes from infected rat lung were prepared for transverse-alternating field effect electrophoresis. Electrophoresis was performed in three stages: stage 1, 30 min at 170 mA with a pulse time of 4 sec; stage 2, 15 hr at 150 mA with a pulse time of 25 sec; stage 3, 7 hr at 170 mA with a pulse time of 35 sec in 0.8% agarose with 10 mM Tris, 0.5 mM EDTA, 4.3 mM acetic acid at 16° C. After electrophoresis, the gel was photographed, exposed to a 302 nm ultraviolet transilluminator for seven minutes, denatured in 0.5 M NaOH, 1.5 M NaCl for one hour, neutralized in 1 M Tris-HCl, pH 8, 1.5 M NaCl and blotted to a HYBOND-N nylon filter in $10 \times SSC$ for 18 hours. The membrane was baked for two hours at 80° C. and prehybridized in 50% formamide, $5 \times$ Denhardt's solution, and $5 \times SSC$ at 42° C. Hybridization was initiated by the addition of $10^5$ cpm/ml of $^{32}$P-labeled 710 bp SalI-SspI fragment containing the entire coding region of *P. carinii* DHFR and continuing incubation at 42° C. for 16 hours. The membrane was washed two times fifteen minutes in $2 \times SSC$ at room temperature, three times fifteen minutes in $0.1 \times SSC$ at 50° C., and exposed to X-ray film.

Expression plasmid construction and characterization of expression products

The coding region from a cDNA clone of *P. carinii* DHFR was amplified using the polymerase-chain reaction technique. The 5' primer was dGGGATCCATATGAATCAGCAAAAGTCTTT which contains nucleotides 1 to 20 and creates BamHl and NdeI sites proximal to the initiation codon. The 3' primer was dGGTCGACAAGCTTTAATATTGAATAAATAGAATAA (complementary to nucleotides 669-689) and creates SalI and HindIII sites. The amplified product was digested with BamHl and HindIII and subcloned into Bluescript to yield pDHFR1. pDHFR1 was sequenced to ensure that the *P. carinii* DHFR coding region was unaltered by the amplification process. A 712 bp SmaI and NdeI fragment of pDHFR1 containing the entire coding region of *P. carinii* DHFR was subcloned into the NdeI-SmaIdigested expression vector pDLTS-Nde, which is described in Davisson et al., *J. Biol. Chem.* (1989) 264:9145-9148 to generate pDLDHFR. This plasmid was introduced into the DHFR-deficient *E. coli* strain D3-157, which is described above. Cells containing pDLDHFR were grown to saturation in LB plus 100 μg/ml ampicillin, collected by centrifugation, resuspended in 100 mM TrisHCl pH 8.0, 1 mM EDTA, and lysed by sonication. Soluble protein extracts were then prepared by centrifugation. Purification of *P. carinii* DHFR was achieved by the passage of crude extracts over methotrexateSepharose and elution with 2 mM dihydrofolate, as described in Grumont et al., *Biochemistry* (1988) 27:3776-3784.

Isolation of *P. carinii* DHFR cDNA sequences

Attempts to isolate *P. carinii* DHFR gene sequences by low-stringency hybridization using a variety of cloned DHFR sequences as probes were unsuccessful, presumably due to the poor conservation of DHFR sequences. As trimethoprim had been shown to be a weak inhibitor of partially purified *P. carinii* DHFR, we isolated *P. carinii* DHFR sequences by their ability to confer trimethoprim resistance to *E. coli*. A plasmid equivalent of a rat *P. carinii* cDNA library cloned into the lambda phage vector ZAP was generated by co-infection of *E. coli* XL-1B cells with the lambda phage library and the replication-defective single-stranded phage R408. This results in the excision of inserts and adjoining plasmid sequences from ZAP recombinants and packaging of their single-stranded equivalents into "phagemids". The supernatant from this infection was heated to inactivate lambda phage and contained $4 \times 10^4$ ampicillin-resistant colony-forming units (cfu) per microliter. Infection of XL-1B with $10^6$ cfu and plating to media containing 100 μg/ml of trimethoprim allowed the isolation of thirty trimethoprim-resistant colonies. Plasmid DNA was isolated from each and used to transform *E. coli* HB101. Two plasmids were found to be capable of transferring trimethoprim resistance. The remainder of the original trimethoprim-resistant clones were presumed to represent chromosomal DHFR mutations.

Sequence of *P. carinii* DHFR cDNA

Restriction analysis of the two plasmids showed substantial overlap, and one was chosen for DNA sequence analysis. The sequence of the entire 900 base pair (bp) insert of ppcDHFRcD was determined (Table 1) and was shown to contain a 618 bp open reading frame. In order to ensure that the DHFR sequence obtained by the direct selection procedure was not altered due to the presence of trimethoprim, independent clones were isolated by nucleic acid hybridization. The coding region of one of these isolates was identical to clones originally obtained by trimethoprim selection.

The predicted start codon of the cDNA conforms poorly to the favorable environment determined for *S. cerevisiae* translational initiation (RxxATGRxxT; Dobson et al., *Nucleic Acids Res.* (1982) 10:2625-2637). The sequences obtained are A-T rich (68% in the coding region; 71% overall). Codon usage is strongly biased toward A or T in third position. Of the 194 codons where a choice between AT or GC in the third position is possible, 168 (87%) are found to contain an A or a T residue.

Characterization of *P. carinii* DHFR gene intron

In order to assess the natural variability of DHFR sequences from different sources of *P. carinii*, specific primers were used in conjunction with the polymerase chain reaction to amplify DHFR coding sequences from DNA isolated from five rat and two human *P. carinii* preparations. The expected amplification product was 712 bp. However, amplification of *P. carinii* genomic DNA revealed a 750 bp product from all sources. This product was subcloned and shown to contain a 43 bp insertion at nucleotide 267 (Table 1). This sequence disrupts the reading frame and demonstrates features consistent with a small intron. The 5' and 3' splice junctions, GCA and TAG, correspond to the consensus sequences for these regions determined in other fungal introns. In addition, the size of the intron is similar to those observed in the *P. carinii* TS gene (45-55 nucleotides). Other than the intron, the only change in the sequence of the 750 bp product was an A to G transition in the 3' untranslated region (position 654).

Characterization of *P. carinii* DHFR linkage to thymidylate synthase

In all protozoa where DHFR has been characterized, it is found as a bifunctional protein with thymidylate synthase (TS-DHFR). In contrast, all other organisms for which these genes have been characterized contain separate TS and DHFR genes and proteins. The *P. carinii* DHFR gene does not encode a bifunctional protein. Furthermore by chromosomal localization (see below), the TS DHFR genes are not linked. The absence of a bifunctional TS-DHFR further supports the conclusion that *P. carinii* is not a member of the Protozoa.

Comparison of *P. carinii* DHFR with other known DHFR sequences

*P. carinii* DHFR genomic sequences predict a protein of 206 amino acids and a molecular weight of 23,868. This size is in accord with the value of 20,000 to 30,000 previously determined by gel filtration of partially purified *P. carinii* DHFR (see Kovacs et al. in *Parasitic Infection* (1988); Leech et al., eds. Churchill Livington, N.Y., pp. 177-193 and, as in *S. cerevisiae*, is slightly larger than mammalian and bacterial DHFRs. In Table 3, the protein sequence is aligned to the DHFR sequences from *Lactobacillus casei*, human *S. cerevisiae*, and *Leishmania major*. Due to the low degree of similarity between DHFRs, alignments in the absence of three-dimensional structures must be somewhat arbitrary. Nonetheless, both primary structure and three-dimensional structure were considered in making these alignments. *P. carinii* DHFR contains those residues that are conserved in all DHFRs (bold letters). The larger size of *P. carinii* DHFR is accounted for primarily by insertions in regions which are loops between known secondary structure elements, as described in Blakeley in *Folates and Pterins: Vol. 1 Chemistry and Bio Chemistry of Folates* (1984) Blakeley et al., eds., John Wiley and Sons, Toronto. However, similar to *S. cerevisiae* DHFR, a particularly large insertion is present near the carboxy terminus (amino acids 181-193). The most dramatic structural differences between bacterial and vertebrate DHFR also occur in this region. A β-sheet (βG in Table 3) in the bacterial enzyme is changed to a "β-bulge" due to a small insertion in the vertebrate enzyme. Whether or not the insertion seen in *P. carinii* DHFR results in a similar structural change or an even more radical change relative to the bacterial enzyme is not known.

TABLE 3

```
                    |--βA--|                                      |---αB------|         |--βB--| |--αC--|
L. casei                          TAFLWAQDRDGLIGKDGHLPW-HLPDDLHYFRAQTV------         -GKIMVVGRRTYESFP      50
H. sapiens                                                                   VGSLNCIVAVSQNMGIGKNGDLPWPPLRNEFRYFQRMTTTSSVEGK-----QNLVIMGKKTWFSIP   63

P. carinii          MNQQKSLTLIVALTTSYGIGRSNSLPW-KLKKEISYFKRVTSFVPTFDSFES--MNVVLMGRKTWESIP                                                              69

MAGGKIPIVGIVACLQPEMGIGFRGGLPW-RLPSEMKYFRQVTSLTKDPNK------KNALIMGRKTWESIP                                              71
S. cerevisiae       MSRAAARFKIPMPETKADFAFPSLRAFSIVVALDMQHGIGDGESIPW-RVPEDMTFFKNQTTLLRNKKPTEKKRNAVVMGRKTWESVP                                       93
L. major

|--βC--|                              |βD|         |--αE---|                 |-βE-|  |------αF-----|
L. casei            --KRPLPERTNVVLTHQEDYQAQG-AVVVH---------- ---DVAAVFAYAKQHPTQ-                  ------ELVIAGGAQIFTAFK------DDVD     111
H. sapiens          EKNRPLKGRINLVLSRELKEPPQGAHFLSR---------S-LDDALKLTEQPELANKVD- -----MVWIVGGSSVYKEAMNH---PGHL                                 130

P. carinii          LQFRPLKGRINVVITRNESLDLGNGIHSAK---------S-LDHALELLYRTYGSESSVQIN-RIFVIGGAQLYKAAMDH--PKLD                                 140

PKFRPLPNRMNVISRSFKDDFVHDKERSI------ -----VQSNSLANAIMNLESNFKEHLE-RIYVIGGGEVYSQIF-----SITD                              136
S. cerevisiae       VKFRPLKGRLNIVLSSKATVEELLAPLPEGQRAAAAQDVVVNGGLAFEAILLARPLYCSSIETAYCVGGAQVYADAMLSPCIEKLQ                              175
L. major

|---βF---|                                       |--βG--|                     |---βG--|    |---βH---|
L. casei            TLLVTRLAGSFEGDT-KMIPLNWDDFTKVSS-              ------RTVEDTNPALTHTYEVWQKKA                                         162
H. sapiens          KLFVTRIMQDFESDT-FFPEIDLEKYKL------            ----LPEYPG---VLSDVQEEKG---IKYKFEVYEKND                                   188

P. carinii          RIMATIIYKDIHCDV-FFPLKFRDKEWSSVWKKEKHSD------------LESWVGTKVPHGKINEDG---FDYEFEMWTRDL                                    206

S. cerevisiae       HWLITKINPLDKNAT-PAMDTFLDAKKLEEVFSEQDPAQLKEFLPKVELPETDC-DQRYSLEEKG----YCFEFTLYNRK                                      211
L. major            EVYLTRIYATAPACTRFFPFPPENAAT------             AWDLASS-QGRRKSEAEG---LEFEICKYVPRN                                       230
```

Chromosomal localization of the P. carinii DHFR gene

It has recently been shown that *P. carinii* contains fourteen chromosomes ranging in size from 295 to 710 kilobase pairs (kbp; see Fishman et al., *J. Protozool.* (1989) 36:4S-5S). In addition, there is a variation of pattern of chromosomes in different isolates. A *P. carinii* DHFR probe was used to probe a filter-replicate of *P. carinii* chromosomes separated by transverse alternating field electrophoresis. Two isolates were shown to have DHFR sequences on a single chromosome of 520 kbp. A third isolate had DHFR sequences on a chromosome of slightly larger molecular weight. The significance of the size variation is unclear, but may be a reflection of strain differences in *P. carinii*. No hybridization to *S. cerevisiae* chromosomes was detected. As *P. carinii* thymidylate synthase is found on a chromosome of 330 kbp, there is no genetic linkage of these proteins.

Expression of P. carinii DHFR in E. coli

Trimethoprim resistance in the original isolates was indicative that functional *P. carinii* DHFR was being synthesized. The total DHFR activity in these isolates was equal to *E. coli* containing vector alone. This small amount of *P. carinii* DHFR is apparently sufficient to overcome the level of trimethoprim used to isolate these clones. However, further work on *P. carinii* DHFR is dependent on the ability to generate sufficient quantities of the enzyme to perform detailed structural and kinetic characterization. In order to enhance the level of expression, the coding region of *P. carinii* DHFR was placed in the expression vector pDLTS-NDe and used to transform the DHFR-deficient *E. coli* strain D3-157. The expression construct was capable of complementing the DHFR deficiency in this strain and significantly increase its growth rate in rich media. Lysates of cells with this construct contain an approximately 25,000 Mr protein not present in cells containing vector alone. *P. carinii* DHFR purified from these cells by methotrexate-Sepharose affinity chromatography comigrates with the 25,000 Mr protein. Enzymatic activity measurements and densitometric scanning of stained gels showed that the level of *P. carinii* DHFR was about 5% of soluble protein in *E. coli* containing the *P. carinii* DHFR expression construct.

Inhibition of recombinant P. carinii DHFR by Trimethoprim

Trimethoprim has been reported to be a weak inhibitor of *P. carinii* DHFR activity in crude homogenates of organisms from rat lung. Use of the purified recombinant enzyme has shown that trimethoprim is a very poor inhibitor of the enzyme. At a dihydrofolate concentration of 25 $\mu$M, the $IC_{50}$ value for trimethoprim was 20,000 nM for the *P. carinii* enzyme. For comparison, the $IC_{50}$ for trimethoprim with human DHFR was 2000 nM and with *E. coli* DHFR, 2 nM. A non-selective inhibitor of DHFR, methotrexate, shows $IC_{50}$ values of about 0.1 nM for all three DHFRs.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated DNA or RNA molecule, which comprises a nucleotide sequence coding for *Pneumocystis carinii* dihydrofolate reductase.

2. The molecule of claim 1, wherein said molecule comprises the dihydrofolate reductase coding sequence:

```
ATG AAT CAG CAA AAG TCT TTA ACA TTG ATT GTT GCA CTT ACA
ACT TCT TAT GGA ATT GGC CGA TCA AAC TCT CTT CCA TGG AAA
TTA AAG AAA GAA ATA AGT TAT TTT AAA CGA GTA ACC TCT TTT
GTA CCA ACT TTT GAT TCA TTT GAA TCG ATG AAT GTT GTA TTG
ATG GGT CGA AAA ACA TGG GAA AGT ATT CCT TTG CAA TTT CGG
CCC CTT AAA GGT CGT ATT AAT GTT GTT ATC ACT CGA AAT GAA
TCT CTG GAT CTA GGA AAT GGA ATT CAT TCT GCA AAA TCC TTG
GAT CAT GCT TTG GAA TTG TTA TAT CGT ACA TAT GGT TCT GAA
AGT TCG GTT CAA ATT AAT CGA ATT TTC GTT ATA GGT GGT GCA
CAG CTA TAT AAA GCA GCT ATG GAT CAT CCT AAA TTA GAT AGA
ATT ATG GCT ACA ATA ATA TAC AAG GAT ATT CAT TGT GAT GTA
TTT TTT CCA CTT AAA TTT AGG GAT AAA GAA TGG TCT TCT GTA
TGG AAA AAA GAA AAA CAT TCA GAT TTA GAA TCT TGG GTT GGT
ACT AAA GTT CCT CAT GGT AAA ATA AAT GAA GAC GGT TTT GAT
TAT GAA TTC GAA ATG TGG ACA AGA GAT TTA TAA
``` or a DNA or RNA sequence encoding the same sequence of amino acids as said coding sequence or a DNA or RNA sequence complementary to said coding sequence with no mismatches between opposed nucleotides.

3. The molecule of claim 2, wherein said molecule is DNA.

4. The molecule of claim 3, wherein said molecule contains said dihydrofolate reductase sequence.

5. The molecule of claim 2, wherein said molecule is RNA and contains a sequence corresponding or complementary to said dihydrofolate reductase sequence.

6. The molecule of claim 1, wherein said sequence is preceded by a functional promoter sequence 5' to said sequence.

7. The molecule of claim 6, wherein at least one copy of said sequence is present in a functioning recombinant DNA or RNA vector.

8. A genetically engineered microorganism, wherein said microorganism comprises the vector of claim 7.

9. The microorganism of claim 8, wherein said microorganism is an *E. coli* strain.

10. An isolated oligonucleotide, comprising at least 10 consecutive nucleotides selected from nucleotide sequences consisting of a first DNA sequence

ATG AAT CAG CAA AAG TCT TTA ACA TTG ATT GTT GCA CTT ACA

ACT TCT TAT GGA ATT GGC CGA TCA AAC TCT CTT CCA TGG AAA

TTA AAG AAA GAA ATA AGT TAT TTT AAA CGA GTA ACC TCT TTT

GTA CCA ACT TTT GAT TCA TTT GAA TCG ATG AAT GTT GTA TTG

ATG GGT CGA AAA ACA TGG GAA AGT ATT CCT TTG CAA TTT CGG

CCC CTT AAA GGT CGT ATT AAT GTT GTT ATC ACT CGA AAT GAA

TCT CTG GAT CTA GGA AAT GGA ATT CAT TCT GCA AAA TCC TTG

GAT CAT GCT TTG GAA TTG TTA TAT CGT ACA TAT GGT TCT GAA

AGT TCG GTT CAA ATT AAT CGA ATT TTC GTT ATA GGT GGT GCA

CAG CTA TAT AAA GCA GCT ATG GAT CAT CCT AAA TTA GAT AGA

ATT ATG GCT ACA ATA ATA TAC AAG GAT ATT CAT TGT GAT GTA

TTT TTT CCA CTT AAA TTT AGG GAT AAA GAA TGG TCT TCT GTA

TGG AAA AAA GAA AAA CAT TCA GAT TTA GAA TCT TGG GTT GGT

ACT AAA GTT CCT CAT GGT AAA ATA AAT GAA GAC GGT TTT GAT

TAT GAA TTC GAA ATG TGG ACA AGA GAT TTA TAA and DNA and RNA sequences encoding the same sequence of amino acids as said first sequence as well as DNA and RNA sequences complementary to said first sequence with no mismatches between opposed nucleotides.

11. The oligonucleotide of claim 10, wherein said oligonucleotide comprises at least 14 consecutive nucleotides.

12. The oligonucleotide of claim 10, wherein said oligonucleotide comprises at least 14 consecutive nucleotides of said first sequence.

* * * * *